United States Patent
Mine et al.

(10) Patent No.: US 6,197,389 B1
(45) Date of Patent: Mar. 6, 2001

(54) FERRIELECTRIC LIQUID CRYSTAL COMPOUND

(75) Inventors: Takakiyo Mine; Masahiro Johno; Tomoyuki Yui, all of Tsukuba (JP)

(73) Assignee: Mitsubishi Gas Chemical Company Inc, Tokyo (JP)

( * ) Notice: Subject to any disclaimer, the term of this patent is extended or adjusted under 35 U.S.C. 154(b) by 0 days.

(21) Appl. No.: 09/351,914

(22) Filed: Jul. 14, 1999

(30) Foreign Application Priority Data

Jul. 24, 1998 (JP) .................................... 10-209363

(51) Int. Cl.$^7$ ........................... C09K 19/12; C07C 69/76; G02F 1/1333
(52) U.S. Cl. .................. 428/1.1; 252/299.65; 349/143; 349/184; 560/76; 560/83
(58) Field of Search ......... 252/299.65; 349/184, 349/174, 143, 172; 560/65, 67, 73, 83, 76; 428/1.1

(56) References Cited

U.S. PATENT DOCUMENTS

| | | | | |
|---|---|---|---|---|
| 5,534,190 | * | 7/1996 | Johno et al. | 252/299.65 |
| 5,716,544 | * | 2/1998 | Motoyama et al. | 252/299.65 |
| 5,728,864 | * | 3/1998 | Motoyama et al. | 560/59 |
| 5,840,209 | * | 11/1998 | Mineta et al. | 252/299.67 |
| 5,938,973 | * | 8/1999 | Motoyama et al. | 252/299.65 |

FOREIGN PATENT DOCUMENTS

| | | |
|---|---|---|
| 0342046 | 11/1989 | (EP) . |
| 0425366 | 5/1991 | (EP) . |
| 829468 | * 3/1998 | (EP) . |
| 0853076 | 7/1998 | (EP) . |
| 885876 | * 12/1998 | (EP) . |
| 0893429 | 1/1999 | (EP) . |
| 11-39541 | * 2/1999 | (JP) . |
| 11-124356 | * 5/1999 | (JP) . |

* cited by examiner

Primary Examiner—Shean C. Wu

(57) ABSTRACT

The present invention provides a ferrielectric liquid crystal compound represented by the following general formula (1),

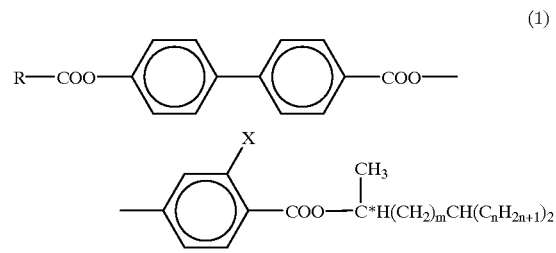

wherein R is a linear alkyl group having of 6 to 12 carbon atoms, X is a hydrogen atom or a fluorine atom, m is an integer of 1 to 3, n is an integer of 1 to 3, and C* is an asymmetric carbon atom.

The ferrielectric liquid crystal compound of the present invention has a ferrielectric phase in a broad temperature range and shows a high speed response in spite of a small spontaneous polarization, and accordingly, it is very useful as a practical raw material for liquid crystal display device.

17 Claims, 1 Drawing Sheet

○ : UP STATE ON THE PLANE
⊗ : DOWN STATE ON THE PLANE

FERRIELECTRIC LIQUID CRYSTAL COMPOUND

FIELD OF THE INVENTION

The present invention relates to a novel ferrielectric liquid crystal compound suitable for use in an active matrix-type liquid crystal display device in which a liquid crystal is driven for each pixel independently of another, and to its use.

PRIOR ART

A liquid crystal display device (LCD) has been being widely used as a flat panel display as a substitute for a conventional display using a Braun tube (CRT), mainly in portable machines and equipment. Along with the recent expansion of the functions of personal computers and word processors and with the recent increase in the capacity of data processing, LCD is also required to have higher functions, that is, to have functions such as a large display capacity, a full-color display, a wide viewing angle, a high-speed response and a high contrast.

As a liquid crystal display method (liquid crystal driving method) to comply with such requirements, there is proposed and practically used an active matrix (AM) display device which works by a method in which thin film transistors (TFT) or diodes (MIM) are formed such that one transistor or diode corresponds to one pixel on a display screen and a liquid crystal is driven for one pixel independently of another.

The above display method has problems in that it is difficult to decrease a cost due to a low production yield and that it is difficult to form a large-sized display screen. Due to a high display quality, however, the above display method is about to surpass an STN display method which has been so far a mainstream and to overtake CRT.

Problems to be Solved by the Invention

However, the above AM display device has the following problems due to the use of a TN (twisted nematic) liquid crystal as a liquid crystal material.

(1) A TN liquid crystal is a nematic liquid crystal, and the response speed is generally low (several tens millisecond (ms)). In the display of video rate, no good image quality can be obtained.

(2) A twisted state (twist alignment) of liquid crystal molecules is used for displaying, and the viewing angle is therefore narrow. In the display with a gray scale in particular, the viewing angle becomes sharply narrowed. That is, the contrast ratio, the color or the like change depending upon viewing angles to a display screen.

For overcoming the above problems, there have been, in recent years, proposed AM panels which use a ferroelectric liquid crystal or an anti-ferroelectric liquid crystal in place of the TN liquid crystal (Japanese Laid-open Patent Publications Nos. 5-249502-A, 5-150257-A and 6-95080-A). However, at present, the following problems remain to solve for the practical use of these liquid crystals.

(3) A ferroelectric liquid crystal has spontaneous polarization. An image sticking is liable to occur due to constant presence of the spontaneous polarization and hence, the driving is made difficult. In the display with a ferroelectric liquid crystal, it is very difficult to perform a gray-scale display since only a binary state of black and white is possible in principle.

For the gray-scale display, a special devising is required (for example, use of a ferroelectric liquid crystal device using monostability; Keiichi NITO et al., SID '94, Preprint, p. 48), and it is required to develop a high technique for practical use.

(4) An anti-ferroelectric liquid crystal is free from the image sticking problem described in the above (3) since it has no permanent spontaneous polarization.

However, in the AM driving, there is needed a liquid crystal material which can be at least driven at 10 V or less. But, the anti-ferroelectric liquid crystal generally shows a high threshold voltage, and its driving at a low voltage is therefore difficult. Further, it has another problem that the gray-scale display is difficult to perform since its optical response involves a hysteresis.

An object of the present invention is to provide a novel material which can overcome the above problems and is suitable for use in AM driving, and a ferrielectric liquid crystal is thinkable as the above novel material.

A ferrielectric phase (Scy* phase) was found for the first time in 4-(1-methylheptyloxy-carbonyl)phenyl-4-(4'-octyloxybiphenyl)carboxylate (called "MHPOBC" for short) that is an anti-ferroelectric liquid crystal compound, in 1989 (Japanese Journal of Applied Physics, Vol. 29, No. 1, 1990, pp. L131–137).

The chemical structural formula and phase transition temperatures (° C.) of the MHPOBC are as follows. Structural formula:

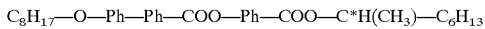

$C_8H_{17}$—O—Ph—Ph—COO—Ph—COO—C*H(CH$_3$)—C$_6$H$_{13}$ wherein Ph is a 1,4-phenylne group and C* is an asymmetric carbon atom.

Phase sequence:

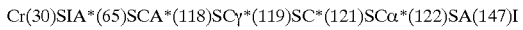

Cr(30)SIA*(65)SCA*(118)SCγ*(119)SC*(121)SCα*(122)SA(147)I wherein Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, and I is an isotropic phase.

DETAILED DESCRIPTION OF THE INVENTION

Figure 1:
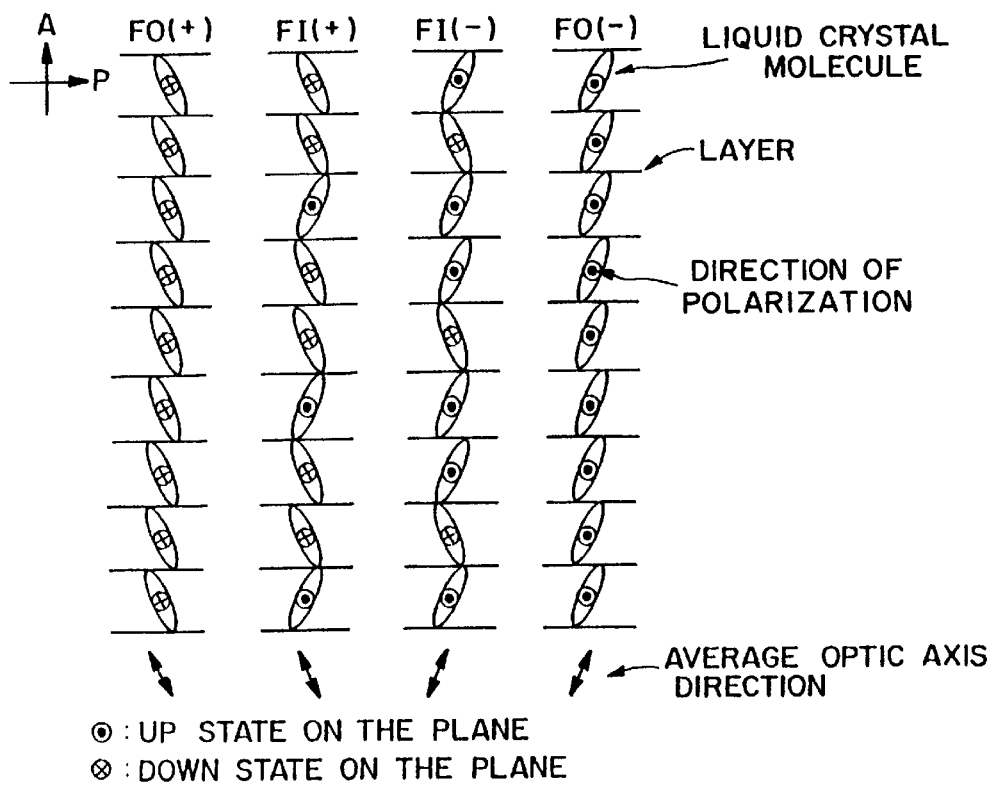
FIG. 1 shows molecular arrangement states of a ferrielectric phase. FI(+) and FI(−) show a ferrielectric state, and FO(+) and FO(−) show an anti-ferroelectric state.

The ferrielectric liquid crystal will be explained by referring to the drawings.

Figure 2:
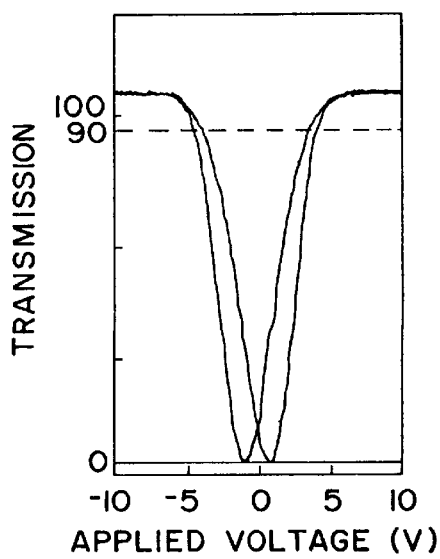
FIG. 2 shows an optical response of a ferrielectric phase to a triangular wave voltage.

For explaining a ferrielectric phase, FIG. 1 shows molecular arrangement states of a ferrielectric phase, and FIG. 2 shows an optical response of a ferrielectric phase to a triangular wave.

A ferrielectric phase has a molecular arrangement state of FI(+) (a case where an applied voltage is positive) or a molecular arrangement state of FI(−) (a case where an applied voltage is negative) as shown in FIG. 1. In a state free of an electric field, FI(+) and FI(−) are equivalent and are therefore co-present.

Therefore, average optic axes are in the direction of a layer normal, and the state is in a dark state under the condition of a polarizer shown in FIG. 1. This state corresponds to a portion where the intensity of transmitted light is 0 at a voltage of 0, in FIG. 2.

Further, though each of FI(+) and FI(−) has spontaneous polarization as is apparent from the molecular arrangement states, the spontaneous polarizations are canceled each other in a state in which these are co-present and consequently, an average spontaneous polarization is zero. This shows that, like an anti-ferroelectric phase, a ferrielectric phase is free from an image sticking phenomenon observed in a ferroelectric phase.

As an electric field is applied to a ferrielectric phase, a region (domain) having an extinguished position appears at a voltage lower than a voltage at which a ferroelectric state is reached. This shows that the above domain has an optic axis in the direction that tilts from the direction of layer normal although the tilt is not so large as that in a ferroelectric state.

The above intermediate state is considered to be FI(+) or FI(−).

As to the liquid crystal compounds in the present invention, a liquid crystal phase which always shows the above intermediate state is called a ferrielectric phase, and a liquid crystal compound having the broadest ferrielectric phase in its phase sequence is called a ferrielectric liquid crystal compound.

When the applied voltage is further increased, the ferrielectric phase causes a phase transition to a ferroelectric phase FO(+) or FO(−) that is a stabilized state, depending upon a direction of the electric field. In FIG. 2, a phase in which the intensity of transmitted light is brought into a saturated state (flat parts on left and right sides) is FO(+) or FO(−).

In the above ferroelectric state FO(+) or FO(−), there is exhibited a spontaneous polarization greater than that in the ferrielectric state FI(+) or FI(−), as is seen in FIG. 1. The response speed increases with an increase in the spontaneous polarization, and as a result, the capability of high speed response is materialized.

Both the ferroelectric states are in a light state under the condition of a polarizer shown in FIG. 1.

A conventional ferroelectric phase provides a switching between FO(+) and FO(−), while the ferrielectric phase has a great characteristic feature that it permits switching among four states of FO(+), FI(+), FI(−) and FO(−).

In the ferrielectric phase, therefore, not a continuous change in the intensity of transmitted light between voltages of 0 V and 4 V but a stepwise change in the intensity of transmitted light ought to be observed.

In FIG. 2, however, a continuous change in the intensity of transmitted light is observed.

It is assumed that the above occurs because the threshold voltage from the co-presence state of FI(+) and FI(−) to FO(+) via FI(+) or the threshold voltage from the co-presence state of FI(+) and FI(−) to FO(−) via FI(−) is not clear.

As shown in FIG. 2, generally, a ferrielectric phase has a tendency that a difference between the voltage required for change from a ferrielectric state to a ferroelectric state and the voltage required for change from a ferroelectric state to a ferrielectric state is small, that is, the width of its hysteresis is very narrow. It characteristically shows an optical response having V-letter-shape and hence, has properties suitable for an active matrix driving (AM driving) and a display with a gray scale in AM driving.

Further, in the ferrielectric phase, the voltage (phase transition voltage) required for a phase change between a ferrielectric state and a ferroelectric state tends to be very small as compared with that of an anti-ferroelectric phase, and it can be therefore said that the ferrielectric phase is suitable for AM driving.

In the ferrielectric phase, generally, the change between the co-presence state of FI(+) and FI(−) and a ferroelectric state (FO(+) or FO(−)) is continuous as shown in FIG. 2, and besides, the voltage required for the change is small. Further, the light transmittance in the co-presence state of FI(+) and FI(−) at an applied voltage of 0 can be further decreased by devising an alignment film.

On the basis of these, in the ferrielectric liquid crystal, the co-presence state of FI(+) and FI(−) can be used as dark, the ferroelectric states FO(+) and FO(−) as light and an intermediate state of these as gray. The display principle thereof uses birefringence of a liquid crystal, and a display device having a decreased viewing angle dependency can be produced as the liquid crystal molecules are arranged in parallel with the substrate surface.

However, the number of ferrielectric liquid crystal compounds that have been synthesized so far is very small, and when application to an AM driving device is taken into account, few ferrielectric liquid crystal compounds that have been already known are satisfactory in respect of hysteresis and a voltage in the phase transition.

Further, in the active matrix driving device, it is an essential problem in practice how large or small the spontaneous polarization of the ferrielectric liquid crystal is.

J. Funfscilling et al. show that in the AM driving, the degree of the voltage required for driving a liquid crystal having spontaneous polarization is in proportion to the spontaneous polarization (Jpn. J. Appl. Phy. Vol. 33, pp 4950 (1994)). It is desirable from the aspect of driving voltage, accordingly, that the spontaneous polarization is as small as possible.

On the other hand, it is thought that the speed (response speed) in the phase transition from a ferrielectric state to a ferroelectric state is largely in proportion to the degree of spontaneous polarization.

It is therefore very advantageous in practice if there can be provided a ferrielectric liquid crystal having a small spontaneous polarization and having a high response speed.

Means to Solve the Problems

Under the circumstances, the present inventors have made studies to find a novel ferrielectric liquid crystal compound having a narrow width of hysteresis, small phase transition voltage, high response speed and accordingly, excellent characteristic properties as an AM driving device, and as a result, the present invention has been arrived at.

That is, according to the present invention, there is provide a ferrielectric liquid crystal compound of the following general formula (1),

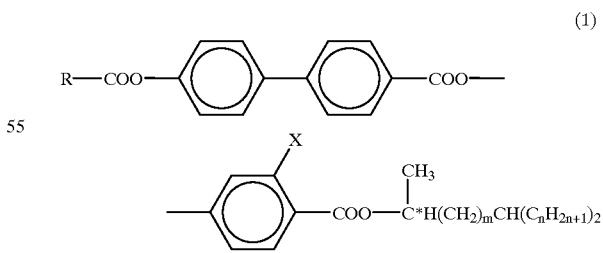

wherein R is a linear alkyl group having 6 to 12 carbon atoms, X is a hydrogen atom or a fluorine atom, m is an integer of 1 to 3, n is an integer of 1 to 3, and C* is an asymmetric carbon atom.

In the ferrielectric liquid crystal compound of the above general formula (1) in the present invention, R is a linear alkyl group having 6 to 12, preferably 9 to 12 carbon atoms. And, X is a hydrogen or a fluorine atom, preferably a fluorine atom, m is an integer of 1 to 3, preferably 2, and n is an integer of 1 to 3, preferably 1.

When the ferrielectric liquid crystal compound of the present invention is considered as a raw material for practical use, the temperature (transition temperature on the high-temperature side) for the transition from an isotropic phase, a smectic A phase or a chiral smectic C phase to a ferrielectric phase is preferably at least 40° C. Further, it is preferable from the practical standpoint that the ferrielectric phase has a temperature range of at least 10° C.

Since the voltage in the phase transition from a ferrielectric state to a ferroelectric state is in proportion to a driving voltage, it is preferably 5 V/μm or less, more preferably 3 V/μm or less in view of the dielectric strength of driving ICs used currently.

Further, it is desirable for the ferrielectric liquid crystal compound of the present invention that a difference between a voltage (phase transition voltage I) in phase transition from the ferrielectric state to the ferroelectric state and a voltage (phase transition voltage II) in phase transition from the ferroelectric state to the ferrielectric state is as small as possible, and it is preferably 0.5 V or lower.

The ferrielectric liquid crystal of the present invention can give an active matrix liquid crystal display device by interposing it between substrates on which non-linear active devices such as thin film transistors or diodes are provided for individual pixels.

An optically active alcohol, $CH_3C^*H(OH)(CH_2)_m(C_nH_{2n+1})_2$, used for the synthesis of the ferrielectric liquid crystal compound of the present invention can be easily produced by the method that the present inventors have already disclosed.

The method of the production thereof, for example, when m is 2 and n is 1, is outlined as follows.

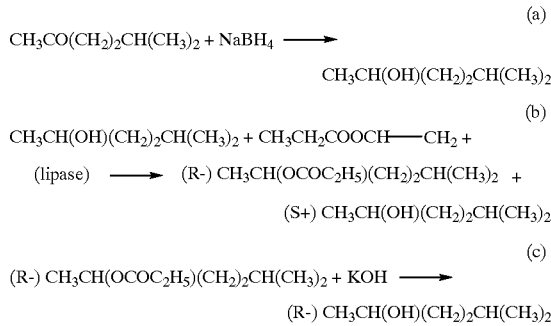

The above method of the production of the optically active alcohol will be briefly explained below.
(a) shows the reduction of 5-methyl-2-hexanone to an alcohol.
(b) shows formation of R-configuration ester by an asymmetric trans-esterification between the alcohol and vinyl propionate.
(c) shows the hydrolysis of the optically resolved ester (b) by an alkali.

Effect of the Invention

The novel ferrielectric liquid crystal compound provided by the present invention has a ferrielectric phase in a broad temperature range and shows a high speed response in spite of a small spontaneous polarization, and accordingly, is very useful as a practical raw material for liquid crystal display devices.

EXAMPLES

The present invention will be explained more in detail with reference to Example hereinafter, while the present invention shall not be limited thereto.

Example 1

(formula (1): R=$C_9H_{19}$, X=F, m=2, n=1 (E1))

Preparation of R-(−)-3-fluoro-4-(1,4-dimethylpentyloxycarbonyl)phenyl-4'-n-decanoyloxybiphenyl-4-carboxylate (1) Preparation of 4-(4'-n-decanoyloxy)biphenylcarboxylic acid 10.0 Grams of 4-(4'-hydroxy)biphenylcarboxylic acid, 9.8 g of n-decanoic acid chloride, 16 ml (millilitre) of triethyl amine and 1 g of dimethylaminopyridine were dissolved in 150 ml of dichloromethane, and the mixture was stirred at room temperature for one day and night.

After completion of the reaction, 50 ml of a 10% hydrochloric acid was added to the reaction mixture and then, the resulting mixture was extracted with 100 ml of ether three times.

The organic phase was washed with 100 ml of a sodium chloride aqueous solution three times and dried over anhydrous sodium sulfate. After distilling off the solvent, the distillate was washed with 400 ml of hexane to obtain an end product.

(2) Preparation of 4-acetoxy-2-fluorobenzoic acid 4.3 Grams of 4-hydroxy-2-fluorobenzoic acid and 8.4 g of acetic anhydride were placed in a two-necked flask and mixed. While the mixture was cooled with water, 5 drops of sulfuric acid were added. After heat generation ended, the mixture was heated at 80° C. for 30 minutes. Thereafter, the reaction mixture was poured into cold water, and a precipitated crystal was recovered by filtration.

The crystal was dried in vacuum, and used in the next step.

(3) Preparation of R-(−)-4-acetoxy-2-fluoro-1-(1,4-dimethylpentyloxycarbonyl)benzene 1.0 Gram of 4-acetoxy-2-fluorobenzoic acid was added to 7 ml of thionyl chloride, and the mixture was allowed to react under reflux for 5 hours.

Then, excessive thionyl chloride was distilled off, and a mixture containing 1 ml of pyridine, 4 ml of dry ether and 0.5 g of R-(−)-5-methylhexan-2-ol was added dropwise.

After the addition, the mixture was stirred at room temperature for one day and night, and diluted with 200 ml of ether, and an organic layer was washed with diluted hydrochloric acid, with a 1N sodium hydroxide aqueous solution and with water in this order, and then dried over magnesium sulfate. The solvent was distilled off, and the resultant crude product was purified through silica gel column chromatography using hexane/ethyl acetate as a solvent, to give an end product.

(4) Preparation of R-(−)-4-hydroxy-2-fluoro-1-(1,4-dimethylpentyloxycarbonyl)benzene 1.0 Gram of the compound obtained in the above (3) was dissolved in 30 ml of ethanol, and 3 g of benzylamine was added dropwise thereto.

Further, the mixture was stirred at room temperature for one day and night, diluted with 300 ml of ether, washed with diluted hydrochloric acid and then with water, and dried over magnesium sulfate.

The solvent was distilled off, and the remainder was subjected to silica gel column chromatography for isolation and purification to give an end product.

(5) Preparation of R-(−)-3-fluoro-4-(1,4-dimethylpentyloxycarbonyl)phenyl-4'-n-decanoyloxybipheyl-4-carboxylate To 1.0 g of the compound obtained in the above (1) was added 10 ml of thionyl chloride, and the mixture was refluxed under heating for 10 hours. Excessive thionyl chloride was distilled off, and 10 ml of pyridine and 25 ml of toluene were added to the mixture. Then, 25 ml of a benzene solution containing 0.8 g of the compound obtained in the above (4) was added dropwise thereto, and the mixture was allowed to react at room temperature for 10 hours.

After completion of the reaction, the reaction mixture was diluted with 300 ml of ether and washed with diluted hydrochloric acid, with a 1N sodium carbonate aqueous solution, and with water in this order, and an organic layer was dried over magnesium sulfate.

Then, the solvent was distilled off, the remainder was isolated by silica gel column chromatography, and ethanol was used for recrystallization, to give an end product.

Table 1 shows $^1$H-NMR spectrum data of the end product obtained in the above Example 1.

Liquid crystal phase was identified as follows, and the results are shown in Table 2.

The liquid crystal was identified for liquid crystal phase by texture observation, conoscopic image observation and DSC (differential scanning calorimeter) measurement. The observation of a conoscopic image is an effective means for identifying a ferrielectric phase. The conoscopic image observation was conducted according to a literature (J. Appl. Phys. 31, 793 (1992)).

Then, the ferrielectric liquid crystal compound obtained in Example 1 was measured for its optical response, and the results are also shown in Table 2. Cells were prepared by the following procedure.

A pair of glass plates with insulating film ($SiO_2$, film thickness; 50 nm) and ITO electrodes were coated with polyimide to a film thickness of about 80 nm, and one of the pair of glass plates was rubbed.

The pair of glass plates were attached to each other through a spacer having a particle diameter of 1.6 μm to form a test cell. The cell had a thickness of 2 μm.

A liquid crystal was heated until the liquid crystal showed an isotropic phase, and the liquid crystal was then injected into the test cell by capillarity. Thereafter, the cell was gradually cooled at a rate of 1° C./minute to align the liquid crystal in parallel.

The light transmittance was defined as follows. The lowest intensity of transmitted light was taken as 0% of light transmittance, and the highest intensity of transmitted light was taken as 100% of light transmittance. The phase transition voltage was defined to be a voltage found at a light transmittance of 90%.

A triangular wave voltage of ±10 V, 5 Hz was applied to the test cell, and a voltage (phase transition voltage I) in the transition from a ferrielectric phase to a ferroelectric phase and a voltage (phase transition voltage II) in the transition from a ferroelectric phase to a ferrielectric phase were obtained at a temperature 10° C. lower than the transition temperature of the ferrielectric phase on a high temperature side.

The spontaneous polarization was determined at a temperature 10° C. lower than the transition temperature of the ferrielectric phase on a high temperature side by applying a triangular wave voltage of 10 V and measuring a polarization inversion current.

The response speed was defined to be a time required for a change from 0% to 90% in the light transmittance, and it was obtained at a temperature 10° C. lower than the transition temperature of the ferrielectric phase on a high temperature side by applying a rectangular wave voltage of 8V, 10 Hz.

Example 2

Preparation of R-(−)-3-fluoro-4-(1,4-dimethylpentyloxycarbonyl)phenyl-4'-n-undecanoyloxybiphenyl-4-carboxylate (formula (1): R=$C_{10}H_{21}$, X=F, m=2, n=1)

An end product was prepared in the same manner as in Example 1 except that the 4-(4'-n-decanoyloxy)biphenylcarboxylic acid was replaced with 4-(4'-n-undecanoyloxy)biphenylcarboxylic acid.

Table 1 shows $^1$H-NMR spectrum data of the end product (5).

Further, the end product was evaluated for a phase transition voltage, a response time, a spontaneous polarization and a phase sequence in the same manner as in Example 1.

Example 3

Preparation of R-(−)-4-(1,4-dimethylpentyloxycarbonyl)phenyl-4'-n-decanoyloxybiphenyl-4-carboxylate (formula (1): R=$C_9H_{19}$, X=H, m=2, n=1)

An end product was prepared in the same manner as in Example 1 except that the 4-acetoxy-2-fluorobenzoic acid was replaced with 4-acetoxybenzoic acid.

Table 1 shows $^1$H-NMR spectrum data of the end product.

Further, the end product was evaluated for a phase transition voltage, a response time, a spontaneous polarization and a phase sequence in the same manner as in Example 1.

Comparative Example 1

Preparation of R-(−)-3-fluoro-4-(1,5-dimethylhexyloxycarbonyl)phenyl-4'-n-decanoyloxybiphenyl-4-carboxylate (formula (1): R=$C_9H_{19}$, X=F, m=3, n=1)

An end product was prepared in the same manner as in Example 1 except that the R-(−)-5-methylhexan-2-ol was replaced with R-(−)-6-methylheptan-2-ol.

Table 1 shows $^1$H-NMR spectrum data of the end product.

Further, the end product was evaluated for a phase sequence in the same manner as in Example 1.

Comparative Example 2

Preparation of R-(−)-3-fluoro-4-(1,3-dimethylbutyloxycarbonyl)phenyl-4'-n-decanoyloxybiphenyl-4-carboxylate (formula (1): R=$C_9H_{19}$, X=F, m=1, n=1)

An end product was prepared in the same manner as in Example 1 except that the R-(−)-5-methylhexan-2-ol was replaced with R-(−)-4-methylpentan-2-ol.

Table 1 shows $^1$H-NMR spectrum data of the end product (5).

Further, the end product was evaluated for a phase sequence in the same manner as in Example 1.

Comparative Example 3

Preparation of R-(−)-3-fluoro-4-(1-methyl-3-ethylpentyloxycarbonyl)phenyl-4'-n-decanoyloxybiphenyl-4-carboxylate (formula (1): R=$C_9H_{19}$, X=F, m=1, n=2)

An end product was prepared in the same manner as in Example 1 except that the R-(−)-5-methylhexan-2-ol was replaced with R-(−)-4-ethylhexan-2-ol.

Table 1 shows $^1$H-NMR spectrum data of the end product (5).

Further, the end product was evaluated for a phase sequence in the same manner as in Example 1.

TABLE 1

|  | Chemical shift (ppm) | | | | | | | | | |
|---|---|---|---|---|---|---|---|---|---|---|
|  | 1H | 2H | 3H | 4H | 5H | 6H | 7H | 8H | 9H | 10H |
| Example 1 | 2.6 | 7.2 | 7.6 | 7.7 | 8.3 | 7.1 | — | 7.1 | 8.0 | 5.2 |
| Example 2 | 2.6 | 7.2 | 7.6 | 7.7 | 8.3 | 7.1 | — | 7.1 | 8.0 | 5.2 |
| Example 3 | 2.6 | 7.2 | 7.6 | 7.7 | 8.3 | 7.3 | 8.2 | 7.3 | 8.2 | 5.2 |
| Comp. Ex. 1 | 2.6 | 7.2 | 7.6 | 7.7 | 8.3 | 7.1 | — | 7.1 | 8.0 | 5.2 |
| Comp. Ex. 2 | 2.6 | 7.2 | 7.6 | 7.7 | 8.3 | 7.1 | — | 7.1 | 8.0 | 5.2 |
| Comp. Ex. 3 | 2.6 | 7.2 | 7.6 | 7.7 | 8.3 | 7.1 | — | 7.1 | 8.0 | 5.2 |

Comp. Ex.: Comparative Example

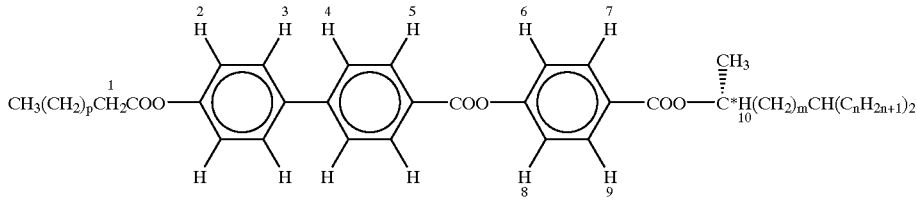

(p is an integer of 4 to 10)

TABLE 2

|  | Phase transition voltage (V/μm) | Response time (μsec) | Spontaneous polarization (nC/cm$^2$) | Phase sequence |
|---|---|---|---|---|
| Example 1 | 1.6 | 49 | 52 | Cr(72)SCγ*(122)SA(140)I |
| Example 2 | 1.7 | 29 | 49 | Cr(37)SCγ*(125)SA(140)I |
| Example 3 | 1.0 | 21 | 51 | Cr(81)SCγ*(116)SA(142)I |
| Comp. Ex. 1 |  |  |  | Cr(60)SCA*(122)SA(138)I |
| Comp. Ex. 2 |  |  |  | Cr(73)SCA*(129)SA(147)I |
| Comp. Ex. 3 |  |  |  | Cr(71)SCA*(114)SA(128)I |

Comp. Ex.: Comparative Example

In the phase sequence of the above Table 2, parenthesized values show phase transition temperatures (° C.), Cr is a crystal phase, SCγ* is a ferrielectric phase, SA is a smectic A phase, SCA* is an anti-ferroelectric phase and I is an isotropic phase.

What is claimed is:

1. A ferrielectric liquid crystal compound of the general formula (1),

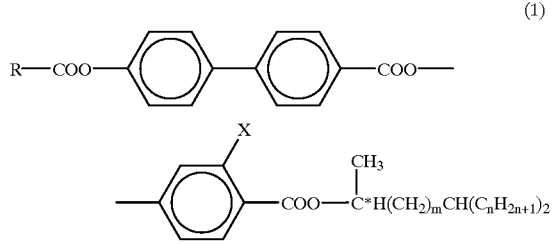

(1)

wherein R is a linear alkyl group having 6 to 12 carbon atoms, X is a hydrogen atom or a fluorine atom, m is an integer of 2 n is an integer of 1 to 3, and C* is an asymmetric carbon atom.

2. The ferrielectric liquid crystal compound of claim 1, wherein in the general formula (1), R is a linear alkyl group having 9 to 12 carbon atoms.

3. The ferrielectric liquid crystal compound of claim 1, wherein in the general formula (1), n is 1.

4. The ferrielectric liquid crystal compound of claim 1, wherein a t ransition temperature of a ferrielectric phase on a high-temperature side is at least 40° C.

5. The ferrielectric liquid crystal compound of claim 1, wherein a difference between a transition temperature of a ferrielectric phase on a high-temperature side and a transition temperature of the ferrielectric phase on a low-temperature side is at least 10° C.

6. The ferrielectric liquid crystal compound of claim 1, wherein a voltage in transition from a ferrielectric state to a ferroelectric state is 5 V/μm or less.

7. The ferrielectric liquid crystal compound of claim 1, wherein a voltage in transition from a ferrielectric state to a ferroelectric state is 3 V/μm or less.

8. The ferrielectric liquid crystal compound of claim 1, which has functions to switch to a co-presence state of two ferrielectric phases, to two ferroelectric phases and to an intermediate state between them by changing the voltage.

9. The ferrielectric liquid crystal compound of claim 1, wherein a difference between a voltage for a change from a ferrielectric state to a ferroelectric state and a voltage for a change from a ferroelectric state to a ferrielectric state is small.

10. An active-matrix liquid crystal display device, in which the ferrielectric liquid crystal of claim 1 is interposed between substrates on which non-linear active devices are provided for individual pixels.

11. A ferrielectric liquid crystal compound of the general formula (1),

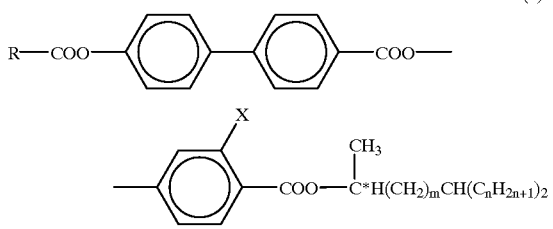 (1)

wherein R is a linear alkyl group having 9 to 12 carbon atoms, X is a hydrogen atom or a fluorine atom, m is an integer of 2, n is an integer of 1 to 3, and C* is an asymmetric carbon atom, having a transition temperature of a ferrielectric phase on a high-temperature side of at least 40° C., and a difference between a transition temperature of a ferrielectric phase on a high-temperature side and a transition temperature of the ferrielectric phase on a low-temperature side is at least 10° C.

12. The ferrielectric liquid crystal compound of claim 11, wherein in the general formula (1), n is 1.

13. The ferrielectric liquid crystal compound of claim 11, wherein a voltage in transition from a ferrielectric state to a ferroelectric state is 3 V/$\mu$m or less.

14. The ferrielectric liquid crystal compound of claim 11, which has functions to switch to a co-presence state of two ferrielectric phases, to two ferroelectric phases and to an intermediate state between them by changing the voltage.

15. The ferrielectric liquid crystal compound of claim 1, wherein R=$C_9H_{19}$, X=F, m=2 and n=1.

16. The ferrielectric liquid crystal compound of claim 1, wherein R=$C_{10}H_{21}$, X=F, m=2 and n=1.

17. The ferrielectric liquid crystal compound of claim 1, wherein R=$C_9H_{19}$, X=H, m=2 and n=1.

* * * * *